United States Patent
Lin et al.

(10) Patent No.: US 11,931,388 B2
(45) Date of Patent: Mar. 19, 2024

(54) POSTBIOTIC EXTRACT AND PREPARATION PROCESS AND USE THEREOF

(71) Applicant: CHAMBIO CO., LTD., Taichung (TW)

(72) Inventors: Meei-Yn Lin, Taichung (TW);
Hung-Pin Chiu, Taichung (TW);
Yi-Heng Chiu, Taichung (TW)

(73) Assignee: CHAMBIO CO., LTD., Taichung (TW)

( * ) Notice: Subject to any disclaimer, the term of this patent is extended or adjusted under 35 U.S.C. 154(b) by 0 days.

(21) Appl. No.: 18/051,968

(22) Filed: Nov. 2, 2022

(65) Prior Publication Data
US 2023/0285479 A1    Sep. 14, 2023

Related U.S. Application Data

(62) Division of application No. 17/037,090, filed on Sep. 29, 2020, now Pat. No. 11,541,085.

(51) Int. Cl.
| | |
|---|---|
| *A61K 35/747* | (2015.01) |
| *A01N 63/20* | (2020.01) |
| *A23L 33/135* | (2016.01) |
| *A61K 35/00* | (2006.01) |
| *A61K 35/741* | (2015.01) |
| *A61K 35/745* | (2015.01) |
| *A61K 39/085* | (2006.01) |
| *A61K 47/36* | (2006.01) |
| *A61K 47/42* | (2017.01) |
| *A61K 35/744* | (2015.01) |

(52) U.S. Cl.
CPC ............ *A61K 35/747* (2013.01); *A01N 63/20* (2020.01); *A23L 33/135* (2016.08); *A61K 35/741* (2013.01); *A61K 35/745* (2013.01); *A61K 39/085* (2013.01); *A61K 47/36* (2013.01); *A61K 47/42* (2013.01); *A23V 2002/00* (2013.01); *A23V 2400/113* (2023.08); *A23V 2400/127* (2023.08); *A23V 2400/517* (2023.08); *A23V 2400/531* (2023.08); *A23V 2400/533* (2023.08); *A61K 2035/115* (2013.01); *A61K 35/744* (2013.01)

(58) Field of Classification Search
None
See application file for complete search history.

(56) References Cited

U.S. PATENT DOCUMENTS

| | | |
|---|---|---|
| 2011/0002902 A1 | 1/2011 | Asada et al. |
| 2020/0093847 A1 | 3/2020 | Buck et al. |

OTHER PUBLICATIONS

Zhou, Hai-Lu, "Isolation of Cell Wall Polysaccharides from Probiotics and Studies on Their Bioactivities", Liaoning University Master's Thesis in Food Engineering, 2017, 2 pages with English translation.
Chang, Yi-Chung, "Race on Probiotics in the Intestinal Tract—Unmissable Opportunity", Mar. 31, 2018, website: https://www.gbimonthly.com/2018/03/21651/, 7 pages with English translation.
Search Report appended to an Office Action, which was issued to Taiwanese counterpart application No. 109115724 by the TIPO dated Nov. 11, 2020, 2 pages with English translation.
Tian et al., "Extraction of Peptidoglycan from *L. paracasei* subp. Paracasei X12 and Its Preliminary Mechanisms of Inducing Immunogenic Cell Death in HT-29 Cells", Int. J. Mol. Sci., 2015, vol. 16, pp. 20033-20049.

*Primary Examiner* — S. Devi

(74) *Attorney, Agent, or Firm* — MH2 TECHNOLOGY LAW GROUP, LLP

(57) ABSTRACT

Disclosed herein is a process for producing a postbiotic extract, which includes providing a first material having a first isoelectric point ranging from pH 1 to pH 6 and a second material having a second isoelectric point ranging from pH 4 to pH 8, admixing the first material and a probiotic microorganism with water having a pH greater than the second isoelectric point, so as to form a mixture, adding the second material into the mixture and then adjusting a pH of the second material-added mixture to between the first and second isoelectric points so that a precipitate is formed, and subjecting the precipitate to a cell wall isolation treatment to obtain the postbiotic extract. Use of the postbiotic extract is also disclosed.

1 Claim, 1 Drawing Sheet

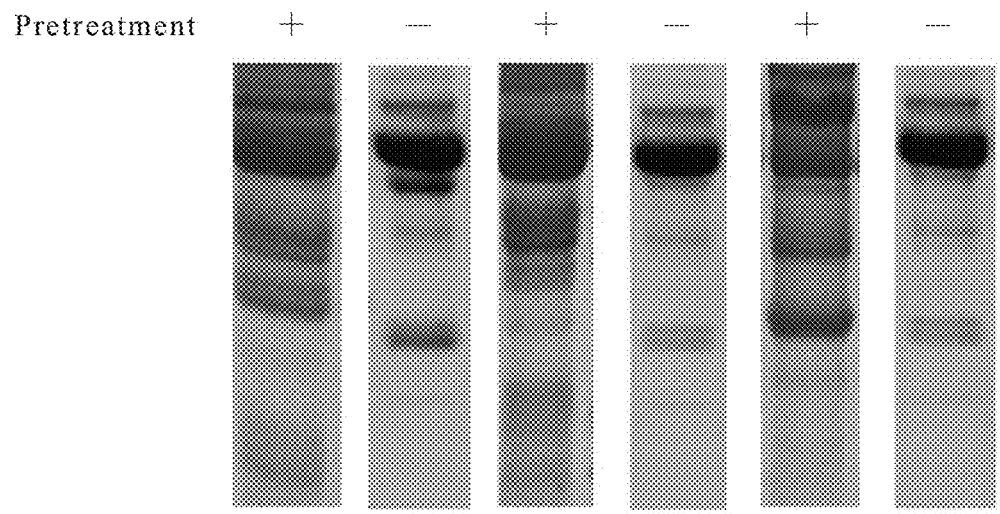
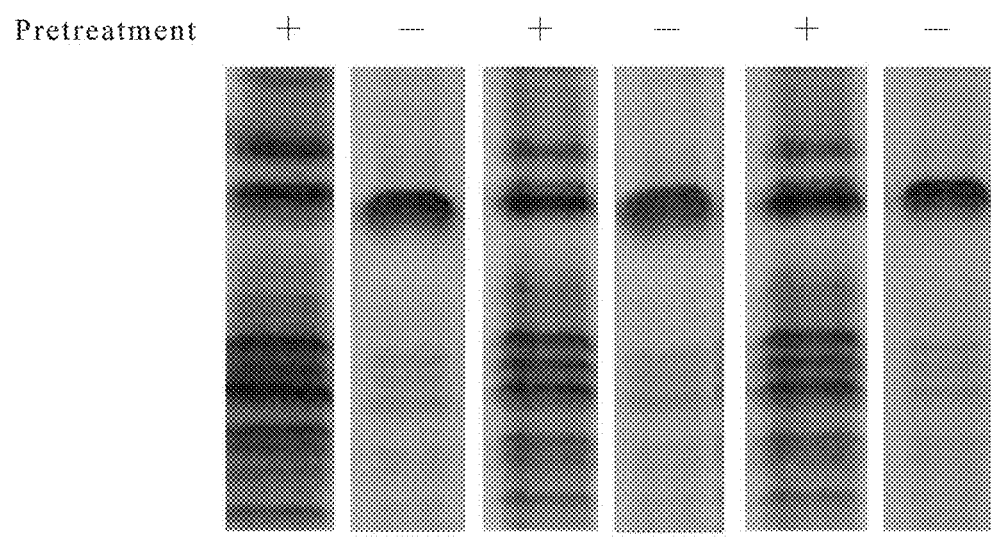

POSTBIOTIC EXTRACT AND PREPARATION PROCESS AND USE THEREOF

CROSS-REFERENCE TO RELATED APPLICATION

This application is a divisional application of U.S. patent application Ser. No. 17/037,090, filed on Sep. 29, 2020, now U.S. patent Ser. No. 11/541,085. The entire content of the prior application is incorporated herein by reference.

FIELD

The present disclosure relates to a postbiotic extract and a process of preparing the same. The present disclosure also relates to use of this postbiotic extract to improve gut health and to inhibit biofilm formation.

BACKGROUND

Probiotics are resident normal flora of the intestinal tract and believed to play important roles in regulating proper intestinal immunity and digestion by balancing intestinal microflora. These beneficial microorganisms are widely used as live microbial dietary supplement and can help restoring intestinal microfloral balance. Many species of lactic acid bacteria (LAB), such as *Lactobacillus* spp., *Lactococcus* spp., *Streptococcus* spp., *Enterococcus* spp., and *Bifidobacterium* spp., are generally considered as probiotics. Furthermore, some of *Bacillus* spp. and some yeasts and *Saccharomyces* spp. have also been found as suitable candidates.

Probiotics are viable by definition, and their stability and viability are considered to be crucial for their health benefits. Paraprobiotics or postbiotics have emerged to denote that non-viable microbial cells, microbial fractions, or cell lysates might also offer physiological benefits to the host by providing additional bioactivity. Postbiotic efficacy is based on the microbial metabolites, proteins, lipids, carbohydrates, vitamins, organic acids, cell wall components, or other complex molecules that are generated in the matrix that is fermented. These postbiotics have drawn attention because of their clear chemical structure, safety dose parameters, long shelf life and the content of various signaling molecules which may have anti-inflammatory, immunomodulatory, anti-obesogenic, antihypertensive, hypocholesterolemic, anti-proliferative, and antioxidant activities.

Postbiotics can be obtained using cell disruption methods, which include heat, enzymatic treatment, solvent extraction, and sonication. However, these methods usually have low extraction efficiency and use large amounts of solvents.

Thus, there is still a need to develop a new method for efficiently producing a postbiotic from a probiotic microorganism.

SUMMARY

Accordingly, in a first aspect, the present disclosure provides a process for producing a postbiotic extract, including the steps of:
a) providing a first material having a first isoelectric point ranging from pH 1 to pH 6, and a second material having a second isoelectric point ranging from pH 4 to pH 8, wherein the second isoelectric point is greater than the first isoelectric point, and the first isoelectric point and the second isoelectric point have a pH difference ranging from 0.5 and 3;
b) admixing the first material and a probiotic microorganism with water having a pH value greater than the second isoelectric point, so as to form a mixture;
c) adding the second material into the mixture, followed by adjusting a pH value of the second material-added mixture to between the first isoelectric point and the second isoelectric point, so that a precipitate is formed; and
d) subjecting the precipitate to a cell wall extraction treatment to obtain the postbiotic extract.

In a second aspect, the present disclosure provides a postbiotic extract which is prepared by a process as described above.

In a third aspect, the present disclosure provides a food product including a postbiotic extract as described above.

Ina fourth aspect, the present disclosure provides a method for inhibiting biofilm formation, which includes applying a postbiotic extract as described above onto an object.

In a fifth aspect, the present disclosure provides a method for improving gut health, which includes administering to a subject a postbiotic extract as described above.

BRIEF DESCRIPTION OF THE DRAWINGS

The above and other objects, features and advantages of the present disclosure will become apparent with reference to the following detailed description and the exemplary embodiments taken in conjunction with the accompanying drawings, in which:

FIG. 1 is a digital image showing a result of sodium dodecyl sulfate-polyacrylamide gel electrophoresis (SDS-PAGE) analysis of postbiotic extracts of Example 1, infra.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a process for producing a postbiotic extract, comprising the steps of:
a) providing a first material having a first isoelectric point ranging from pH 1 to pH 6, and a second material having a second isoelectric point ranging from pH 4 to pH 8, wherein the second isoelectric point is greater than the first isoelectric point, and the first isoelectric point and the second isoelectric point have a pH difference ranging from 0.5 and 3;
b) admixing the first material and a probiotic microorganism with water having a pH value greater than the second isoelectric point, so as to form a mixture;

c) adding the second material into the mixture, followed by adjusting a pH value of the second material-added mixture to between the first isoelectric point and the second isoelectric point, so that a precipitate is formed; and d) subjecting the precipitate to a cell wall extraction treatment to obtain the postbiotic extract.

According to the present disclosure, the probiotic microorganism may be selected from the group consisting of *Bacillus* spp., *Streptococcus* spp., *Lactococcus* spp., *Abiotrophia* spp., *Aerococcus* spp., *Carnobacterium* spp., *Enterococcus* spp., *Lactobacillus* spp., *Leuconostoc* spp., *Oenococcus* spp., *Pediococcus* spp., *Tetragenococcus* spp., *Vagococcus* spp., *Weissella* spp., *Bifidobacterium* spp., *Saccharomyces* spp., *Kluyveromyces* spp., *Staphylococcus* spp., *Pediococcus* spp., *Propionibacterium* spp., and combinations thereof.

According to the present disclosure, the *Lactobacillus* spp. may be selected from the group consisting of *Lactobacillus plantarum, Lactobacillus acidophilus, Lactobacillus casei, Lactobacillus rhamnosus, Lactobacillus paracasei*, and combinations thereof.

According to the present disclosure, the *Bifidobacterium* spp. may be selected from the group consisting of *Bifidobacterium bifidum, Bifidobacterium lactis, Bifidobacterium longum, Bifidobacterium breve, Bifidobacterium animalis*, and combinations thereof.

According to the present disclosure, the *Bacillus* spp. may be selected from the group consisting of *Bacillus coagulans, Bacillus subtilis, Bacillus clausii*, and combinations thereof.

According to the present disclosure, the probiotic microorganism may be alive or dead, concentrated or non-concentrated, or in the form of a liquid, a paste, a semi-solid, or a solid (e.g. a pellet, a granule, or a powder), and may be heat-inactivated, frozen, dried, or freeze-dried (for example, may be in a freeze-dried form or a spray/fluid bed dried form). In an exemplary embodiment, the probiotic microorganism is heat-inactivated and is in a spray-dried powder form.

According to the present disclosure, the heat inactivation of the probiotic microorganism may be conducted at 60° C. to 140° C. for 1 second to 30 minutes. In an exemplary embodiment, the heat inactivation is conducted at 73±2° C. for 15 seconds.

According to the present disclosure, the first material may be selected from the group consisting of nonfat dry milk, casein, whey proteins, soybean proteins, pea proteins, egg proteins, rice proteins, hydrolyzed proteins, corn proteins, wheat proteins, barley proteins, gelatin, collagen, amino acids (for instance, branched chain amino acids), chitosan, chitin, and combinations thereof. In an exemplary embodiment, the first material is a whey protein.

According to the present disclosure, the second material may be selected from the group consisting of sodium alginate, agar, carrageenan, pectin, arabic gum, xanthan gum, locust bean gum, starch (such as modified starch), trehalose, dextrin (such as resistant maltodextrin), syrup, guar gum, konjac powder, vegetable fiber, synthetic fiber, semi-synthetic fiber, and combinations thereof. In an exemplary embodiment, the second material is dextrin.

In an exemplary embodiment of the present disclosure, the first isoelectric point and the second isoelectric point have a pH difference of 0.8.

According to the present disclosure, the precipitate may be obtained by methods well known in the art, including but not limited to centrifugation, filtration, and gravity settling. In an exemplary embodiment, the precipitate is obtained by filtration.

As used herein, the terms "isolation treatment" and "extraction treatment" can be used interchangeably, and mean that a cell wall component or a microbial metabolite is to be separated from a cell wall, in which it was originally present, through a treatment.

According to the present disclosure, the procedures and conditions of the cell wall isolation treatment are within the expertise and routine skills of those skilled in the art (for example, see Pei-Jun Tian et al. (2015), *Int. J. Mol. Sci.*, 16(8): 20033-20049).

The present disclosure also provides a postbiotic extract which is prepared by a process as described above.

The present disclosure also provides a food product, which includes a postbiotic extract as described above. According to the present disclosure, for preparing the food product, the postbiotic extract may be incorporated into an edible material using a standard technique well known to one of ordinary skill in the art. For instance, the aforesaid postbiotic extract may be directly added to the edible material, or may be utilized for preparing an intermediate composition (e.g., a food additive or a premix) suitable to be subsequently added to the edible material.

According to the present disclosure, the food product may be in the form of fermented foods, processed foods, health foods, or dietary supplements.

The food product according to the present disclosure may further include at least one probiotic microbe. As used herein, the terms "probiotic microbe" and "probiotic" are used interchangeably, and refer to preparations microorganisms of live microorganisms. These microorganisms may remain and survive in the gastrointestinal tract after ingested by an animal, and can exert a desired effect (e.g. gut microbiota modifying effect, preventive or therapeutic effect, etc.).

Probiotic microorganisms suitable for use in the present disclosure include, but are not limited to, a *Lactobacillus* sp., a *Enterococcus* sp., a *Streptococcus* sp., a *Pediococcus* sp., a *Bacillus* sp., a *Bifidobacterium* sp., yeasts, and their combinations.

According to the present disclosure, the food product may further comprise an additional food additive selected from the group consisting of starch, dextrin, lactose, maize flour, rice flour, tricalcium phosphate, silicon dioxide, magnesium stearate, calcium carbonate, glucose, sucrose, fructose, sugar alcohol, oligosaccharides, sugar substitutes, fruit juice powder, yeast powder, nonfat dry milk, casein, whey proteins, amino acids, citric acid, citrate, lactic acid, lactate, nucleotides, and their combinations.

In addition, the postbiotic extract according to the present invention may be prepared in the form of a pharmaceutical composition.

According to the present disclosure, the pharmaceutical composition may be formulated into a suitable dosage form for parenteral, oral or topical administration using technology well known to those skilled in the art. The suitable dosage form includes, but is not limited to, sterile powder, tablets, troches, lozenges, pellets, capsules, dispersible powder or granules, solutions, suspensions, emulsions, syrup, elixir, slurry, external preparations, and the like.

The pharmaceutical composition according to the present disclosure may further include a pharmaceutically acceptable carrier widely employed in the art of drug-manufacturing. For instance, the pharmaceutically acceptable carrier may include one or more of the following agents: solvents, buffers, suspending agents, decomposers, disintegrating agents, dispersing agents, binding agents, excipients, stabilizing agents, chelating agents, diluents, gelling agents, preservatives, lubricants, absorption delaying agents, liposomes, and the like. The choice and amount of the aforesaid agents are within the expertise and routine skills of those skilled in the art.

The present disclosure also provides a method for inhibiting biofilm formation, which includes applying a postbiotic extract as described above onto an object.

As used herein, the term "biofilm formation" refers to the attachment of microorganisms to surfaces and the subsequent development of multiple layers of cells.

As used herein, the term "inhibition" or "inhibiting" refers to a decrease of biofilm associated microorganism formation and/or growth. The microorganisms may include gram-positive or gram-negative bacteria, yeasts, and fungi.

According to the present disclosure, the object may be a medical device, a medical instrument, a dressing, a bandage, a food preparation surface, a food packaging surface, a manufacturing surface, a consumer good, a water treatment system, a water delivery system, or a ventilation system.

In certain embodiments, the object may be selected from the group consisting of a denture, a mouth guard, a dairy line, a water line, an adhesive bandage, a component of an HVAC (heating, ventilation, and air-conditioning) system, a component of a water treatment facility, a component of a vacuum or a vacuum cleaner, a vacuum cleaner bag, a vacuum cleaner filter, an air filter, a component of a cooling tower, a toy, a window, a door, a window frame, a doorframe, a medical instrument, a dental instrument, a bathroom tile, a kitchen tile, food industry processing instruments, hospital tables and beds, an animal water dish, a washing machine, a dish washer, a towel, a dish, a bowl, a utensil, a cup, a glass, a cutting board, a dish drying tray, a whirlpool bathtub, a sink, a toilet, a toilet seat, a swimming pool, a birdbath, a planter, a garden hose, a fish pond, an oil pipe, a gas pipe, a dairy line filter, a line used in food and beverage manufacturing, a cosmetic container, an outdoor pond liner, a tap and water spout, a humidifier, a humidifier filter, a bathroom tile, a bathroom fixture, a toilet lid, a swimming pool liner, a swimming pool skimmer, a swimming pool filter, a hot tub line, a hot tub filter, a washing machine liner, a dishwasher liner, an animal water dish, a food storage container, a beverage storage container, a plate, a cup, a fork, a knife, a spoon, a garbage bag, and a counter top.

According to the present disclosure, biofilm formation may be caused by a microbe selected from the group consisting of *Campylobacter* spp., *Clostridium perfringens*, *Escherichia coli*, *Listeria monocytogenes*, *Vibrio cholerae*, *Salmonella* spp., *Staphylococcus* spp., and combinations thereof.

Examples of the *Staphylococcus* spp. include, but are not limited to, *Staphylococcus aureus*, *Staphylococcus epidermidis*, *Staphylococcus agalactiae*, *Staphylococcus saprophyticus*, *Staphylococcus haemolyticus*, *Staphylococcus warneri*, *Staphylococcus hominis*, *Staphylococcus simulans*, *Staphylococcus lugdunensis*, *Staphylococcus schleiferi*, *Staphylococcus capitis*, *Staphylococcus caprae*, *Staphylococcus pasteuri*, *Staphylococcus cohnii*, *Staphylococcus xylosus*, and *Staphylococcus saccharolyticus*.

The present disclosure also provides a method for improving gut health, which includes administering to a subject a postbiotic extract as described above.

As used herein, the term "improving gut health" means that an individual, upon treatment with the postbiotic extract, exhibits a healthy gut/intestinal microbiota, which is beneficial for human or animal health and suitable for a maintenance and/or an improvement of the digestion of said individual. Such a healthy gut/intestinal microbiota is ultimately linked to proper nutrient absorption, adequate growth, less colic, less infection, less diarrhea, and the best gut health.

The disclosure will be further described by way of the following examples. However, it should be understood that the following examples are solely intended for the purpose of illustration and should not be construed as limiting the disclosure in practice.

EXAMPLES

General Experimental Materials:
1. The probiotics used in the following experiments are listed in Table 1.

TABLE 1

| Bacteria | Strain | Source |
| --- | --- | --- |
| *Lactobacillus* spp. | *Lactobacillus plantarum* CB102<br>*Lactobacillus acidophilus* JCM1132<br>*Lactobacillus casei* JCM1134 | Department of<br>Food Science<br>and<br>Biotechnology,<br>National Chung<br>Hsing |
| *Bifidobacterium* spp. | *Bifidobacterium bifidum* JCM1255<br>*Bifidobacterium lactis* JCM10602<br>*Bifidobacterium longum* CB108 | University,<br>Taiwan |
| *Bacillus* spp. | *Bacillus coagulans* CB106 | |

2. Human colon adenocarcinoma cell line Caco-2 was purchased from the Bioresource Collection and Research Center of the Food Industry Research and Development Institute (BCRC of FIRDI, Taiwan). Caco-2 cells were grown in a 10-cm Petri dish containing Dulbecco's Modified Eagle's Medium (DMEM) (Thermo Fisher Scientific) supplemented with 10% fetal bovine serum (FBS). The Caco-2 cells were cultivated in an incubator with culture conditions set at 37° C. and 5% $CO_2$. Medium change was performed every two to three days. Cell passage was performed when the cultured cells reached 80%-90% of confluence.

General Procedures:
1. Determination of transforming growth factor-$\beta$ (TGF-$\beta$) content The TGF-$\beta$ content was determined using an enzyme-linked immunosorbent assay (ELISA) kit (Cat. No. 559119, BD Biosciences) in accordance with the manufacturer's instructions.

Example 1. Preparation of Postbiotic Extract of Present Disclosure

A respective one of *Lactobacillus plantarum* CB102 (deposited at the Deutsche Sammlung von Mikroorganismen und Zellkulturen (DSMZ) GmbH (Inhoffenstraße 7B, 38124 Braunschweig, Germany) under an accession number DSM 33894 on 6 Sep. 2021 in accordance with the Budapest Treaty), *Lactobacillus acidophilus* JCM1132, *Lactobacillus casei* JCM1134, *Bifidobacterium bifidum* JCM1255, *Bifidobacterium lactis* JCM10602, and *Bifidobacterium longum* CB108 (deposited at the Deutsche Sammlung von Mikroorganismen und Zellkulturen (DSMZ) GmbH (Inhoffenstraße 7B, 38124 Braunschweig, Germany) under an accession number DSM 33895 on 6 Sep. 2021 in accordance with the Budapest Treaty) was inoculated in a Lactobacilli MRS broth (BD DIFCO, Cat. No. DF0881-17-5), and was then cultivated in an incubator (37° C., 5% $CO_2$) for 16 hours. The respective resultant culture was inactivated by high-temperature short-time (HTST) pasteurization (73±2° C., 15 seconds), followed by centrifugation at 10,000 rpm and 25° C. for 15 minutes. The resultant cell pellet was collected, followed by spray-drying. A portion of the respective dried bacterial cell powder was subjected to a pretreatment as follows.

A suitable amount of whey protein having an isoelectric point of 4.4 (NZMP, Cat. No. WPC80) was dissolved in water, and the resultant 10% whey protein solution (w/v, g/L) was adjusted to pH 7.5 through addition of sodium carbonate, followed by adding a suitable amount of a respective one of the six dried bacterial cell powders obtained above under agitation to reach a final concentration of 5% (w/v, g/L). Thereafter, dextrin having an isoelectric point of 5.2 (ZHUCHENG DONGXIAO, Cat. No. Malto-dextrin DE8-10) was slowly added into the resultant mixture to reach a final concentration of 6% (w/v, g/L), followed by adjusting the dextrin-added mixture to a pH of 4.8 using lactic acid, so that a precipitate was formed due to charge neutralization. Filtration was conducted using a filter paper having a pore size of 25 μm, so as to obtain the precipitate. The precipitate was subjected to a spray drying treatment, thereby obtaining a pretreated bacterial cell powder.

The isolation and extraction of the cell wall of each pretreated bacterial cell powder was conducted using a method slightly modified from that described by Pei-Jun Tian et al. (2015), *Int. J. Mol. Sci.*, 16 (8): 20033-20049. Briefly, 50 mg of the respective pretreated bacterial cell powder was mixed with 1 mL of 10% lactic acid, followed by heating in a water bath incubator (80° C.) for 60 minutes. After centrifugation at 10,000 g for 15 minutes, the resultant pellet was collected and was mixed with 1 mL of a solution containing a 0.5 M citrate solution and ethanol (4:10, v/v, pH 4.6), followed by incubation overnight. After centrifugation at 10,000 g for 20 minutes, the pellet thus obtained was washed with 95% ethanol, followed by heating in a dry bath incubator (80° C.) for 40 minutes to remove ethanol. Thus, a postbiotic extract was obtained. The resultant postbiotic extract was used for the following example and is referred to as "the postbiotic extract of the present disclosure" hereinafter.

In addition, for the sake of comparison, another portion of the respective one of the six dried bacterial cell powders, which was not pretreated according to the procedures described above, was subjected to the same isolation and extraction processes. The postbiotic extract thus obtained was used for the following example and is referred to as "the postbiotic extract of the prior art" hereinafter.

Example 2. Analysis of Extraction Yield and Protein Content

In order to determine the extraction yield and the protein content, the postbiotic extract of the present disclosure and the postbiotic extract of the prior art obtained in Example 1 were subjected to the following analyses.

A. Determination of Extraction Yield

The weight of each of the twelve postbiotic extracts was recorded. The extraction yield (%) of the respective postbiotic extract was calculated using the following Equation (I):

$$A = (B/50) \times 100 \qquad (I)$$

where A=extraction yield (%)

B=weight of respective postbiotic extract (mg)

The result is shown in Table 2 below. It can be seen from Table 2 that the extraction yields of the six postbiotic extracts of the present disclosure were significantly higher than those of the six postbiotic extracts of the prior art, indicating that the process of the present disclosure can effectively produce postbiotic extracts from probiotics.

TABLE 2

| | Extraction yield (%) | |
|---|---|---|
| Strain | The postbiotic extract of the present disclosure | The postbiotic extract of the prior art |
| *Lactobacillus plantarum* CB102 | 43.34% | 21.40% |
| *Lactobacillus acidophilus* JCM1132 | 44.14% | 20.54% |
| *Lactobacillus casei* JCM1134 | 43.94% | 21.11% |
| *Bifidobacterium bifidum* JCM1255 | 30.97% | 15.44% |
| *Bifidobacterium lactis* JCM10602 | 31.24% | 15.83% |
| *Bifidobacterium longum* CB108 | 31.82% | 16.75% |

B. Determination of Protein Content

The respective postbiotic extract was dissolved in a phosphate buffer solution (containing 8 g/L NaCl, 0.2 g/L KCl, 1.44 g/L $Na_2HPO_4$, and 0.24 g/L $KH_2PO_4$, and having a pH of 6.2), followed by determining the protein content with Pierce™ BCA Protein Assay Kit (Thermo Scientific, Cat. No. 23225) according to the manufacturer's instructions.

The result is shown in Table 3 below. It can be seen from Table 3 that the protein contents of the six postbiotic extracts of the present disclosure were significantly higher than those of the six postbiotic extracts of the prior art.

TABLE 3

| | Protein content | |
|---|---|---|
| Strain | The postbiotic extract of the present disclosure | The postbiotic extract of the prior art |
| *Lactobacillus plantarum* CB102 | 0.39% | 0.20% |
| *Lactobacillus acidophilus* JCM1132 | 0.41% | 0.21% |
| *Lactobacillus casei* JCM1134 | 0.40% | 0.20% |
| *Bifidobacterium bifidum* JCM1255 | 1.40% | 0.69% |
| Bifidobacterium *lactis* JCM10602 | 1.38% | 0.67% |
| *Bifidobacterium longum* CB108 | 1.35% | 0.70% |

C. Sodium Dodecyl Sulfate-Polyacrylamide Gel Electrophoresis (SDS-PAGE) Analysis 1 g of the respective postbiotic extract was dissolved in 20 mL of water, followed by performing SDS-PAGE analysis using an electrophoresis system (Bio-Rad).

Referring to FIG. 1, the band intensities of the six postbiotic extracts of the present disclosure were significantly higher than those of the six postbiotic extracts of the prior art. The results of this example indicate that the process of the present disclosure is effective in producing a postbiotic extract from bacterial cells, and the resultant postbiotic extract contains high levels of cell wall components (such as peptidoglycan, lipoteichoic acid, teichoic acid, glycoprotein, and proteoglycan).

Example 3. Evaluation for Inhibition Effect of Postbiotic Extract According to this Disclosure on Biofilm Formation of *Staphylococcus aureus*

Experimental Procedures:

*Staphylococcus aureus* was inoculated into a tryptic soy broth (TSB) (BD Bacto™, Cat. No. DF0370-17-3), followed by cultivation in an incubator (37° C., 5% $CO_2$) for 16 hours. The resultant culture was divided into 17 groups, including one control group, eight comparative groups (i.e., comparative groups L-1 to L-4 and B-1 to B-4), and eight experimental groups (i.e., experimental groups L-1 to L-4 and B-1 to B-4). The culture of each group was incubated in a respective well of a 96-well culture plate at a cell number of $1 \times 10^{10}$ CFU/L. Thereafter, each of the cultures of the eight comparative groups and eight experimental groups was treated with the respective test postbiotic extract so that the culture of each group had a final concentration of the respective test postbiotic extract as shown in Table 4. The culture of the control group received no treatment.

TABLE 4

| Group | Test postbiotic extract | Final concentration (mg/L) |
|---|---|---|
| Control group | — | 0 |
| Comparative group L-1 | The postbiotic extract of the prior art from *Lactobacillus plantarum* CB102 | 25 |
| Comparative group L-2 | | 50 |
| Comparative group L-3 | | 100 |
| Comparative group L-4 | | 200 |
| Experimental group L-1 | The postbiotic extract of the present disclosure from *Lactobacillus plantarum* CB102 | 25 |
| Experimental group L-2 | | 50 |
| Experimental group L-3 | | 100 |
| Experimental group L-4 | | 200 |
| Comparative group B-1 | The postbiotic extract of the prior art from *Bifidobacterium longum* CB108 | 25 |
| Comparative group B-2 | | 50 |
| Comparative group B-3 | | 100 |
| Comparative group B-4 | | 200 |
| Experimental group B-1 | The postbiotic extract of the present disclosure from *Bifidobacterium longum* CB108 | 25 |
| Experimental group B-2 | | 50 |
| Experimental group B-3 | | 100 |
| Experimental group B-4 | | 200 |

Each group was cultivated in an incubator (37° C., 5% $CO_2$) for 24 hours. The liquid in each well was removed, followed by washing with phosphate-buffered saline (PBS). Thereafter, 100 µL of 95% ethanol was added into each well, followed by incubating at room temperature for 10 minutes, and the resultant fixed cells were then stained with 100 µL of 0.1% crystal violet for 15 minutes. The liquid in each well was removed, followed by washing with PBS. Thereafter, 200 µL of 10% acetic acid was added into each well, followed by incubating at room temperature for 10 minutes, so as to solubilize crystal violet. The resultant biofilm contained in each well was subsequently subjected to determination of absorbance at a wavelength of 590 nm by a spectrophotometer.

The inhibition rate (%) was calculated using the following Equation (II):

$$C = (1 - D/E) \times 100 \quad (II)$$

where C=inhibition rate (%)
D=$OD_{590}$ value of the respective experimental group or comparative group
E=$OD_{590}$ value of the control group Results:

Table 5 shows the inhibition rate of each group. It can be seen from Table 5 that the inhibition rates determined in the experimental groups L-1 to L-4 were respectively higher than those determined in the comparative groups L-1 to L-4, and the inhibition rates determined in the experimental groups B-1 to B-4 were also respectively higher than those determined in the comparative groups B-1 to B-4. Therefore, the applicant contemplates that the postbiotic extract of the present disclosure is effective in inhibiting biofilm formation.

TABLE 5

| Group | Postbiotic extract | Inhibition rate (%) |
|---|---|---|
| Control group | — | 0% |
| Comparative group L-1 | The postbiotic extract of the prior art from *Lactobacillus plantarum* CB102 | 6.9% |
| Comparative group L-2 | | 21.3% |
| Comparative group L-3 | | 40.5% |
| Comparative group L-4 | | 41.2% |
| Experimental group L-1 | The postbiotic extract of the present disclosure from *Lactobacillus plantarum* CB102 | 10.2% |
| Experimental group L-2 | | 30.6% |
| Experimental group L-3 | | 61.2% |
| Experimental group L-4 | | 63.2% |
| Comparative group B-1 | The postbiotic extract of the prior art from *Bifidobacterium longum* CB108 | 0.7% |
| Comparative group B-2 | | 8.1% |
| Comparative group B-3 | | 19.7% |
| Comparative group B-4 | | 29.1% |
| Experimental group B-1 | The postbiotic extract of the present disclosure from *Bifidobacterium longum* CB108 | 1.0% |
| Experimental group B-2 | | 10.2% |
| Experimental group B-3 | | 27.5% |
| Experimental group B-4 | | 36.6% |

Example 4. Evaluation for the Effect of Postbiotic Extract According to this Disclosure on Restoring Healthy Gut Flora Experimental Procedures:

*Staphylococcus aureus* and a respective one of *Lactobacillus plantarum* CB102, *Lactobacillus acidophilus* JCM1132, *Lactobacillus casei* JCM1134, *Bifidobacterium bifidum* JCM1255, *Bifidobacterium lactis* JCM10602, *Bifidobacterium longum* CB108, and *Bacillus coagulans* CB106 were inoculated in a TSB, followed by cultivation in an incubator (37° C., 5% $CO_2$) for 8 hours. The respective resultant co-culture was divided into 4 groups (including one control group, one comparative group, and two experimental groups), and each group was treated with a test sample as shown in Table 6.

TABLE 6

| Co-culture | Groups | Test sample | Final concentration |
|---|---|---|---|
| Co-culture of *Staphylococcus aureus* and *Lactobacillus acidophilus* JCM1132 | Control group 1 | — | — |
| | Comparative group 1 | Inulin | 5 g/L |
| | Experimental group 1-L | The postbiotic extract of the present disclosure from *Lactobacillus plantarum* CB102 | 100 mg/L |
| | Experimental group 1-B | The postbiotic extract of the present disclosure from *Bifidobacterium longum* CB108 | 200 mg/L |

TABLE 6-continued

| Co-culture | Groups | Test sample | Final concentration |
|---|---|---|---|
| Co-culture of Staphylococcus aureus and Lactobacillus casei JCM1134 | Control group 2 | — | — |
| | Comparative group 2 | Inulin | 5 g/L |
| | Experimental group 2-L | The postbiotic extract of the present disclosure from Lactobacillus plantarum CB102 | 100 mg/L |
| | Experimental group 2-B | The postbiotic extract of the present disclosure from Bifidobacterium longum CB108 | 200 mg/L |
| Co-culture of Staphylococcus aureus and Lactobacillus plantarum CB102 | Control group 3 | — | — |
| | Comparative group 3 | Inulin | 5 g/L |
| | Experimental group 3-L | The postbiotic extract of the present disclosure from Lactobacillus plantarum CB102 | 100 mg/L |
| | Experimental group 3-B | The postbiotic extract of the present disclosure from Bifidobacterium longum CB108 | 200 mg/L |
| Co-culture of Staphylococcus aureus and Bifidobacterium lactis JCM10602 | Control group 4 | — | — |
| | Comparative group 4 | Inulin | 5 g/L |
| | Experimental group 4-L | The postbiotic extract of the present disclosure from Lactobacillus plantarum CB102 | 100 mg/L |
| | Experimental group 4-B | The postbiotic extract of the present disclosure from Bifidobacterium longum CB108 | 200 mg/L |
| Co-culture of Staphylococcus aureus and Bifidobacterium bifidum JCM1255 | Control group 5 | — | — |
| | Comparative group 5 | Inulin | 5 g/L |
| | Experimental group 5-L | The postbiotic extract of the present disclosure from Lactobacillus plantarum CB102 | 100 mg/L |
| | Experimental group 5-B | The postbiotic extract of the present disclosure from Bifidobacterium longum CB108 | 200 mg/L |
| Co-culture of Staphylococcus aureus and Bifidobacterium longum CB108 | Control group 6 | — | — |
| | Comparative group 6 | Inulin | 5 g/L |
| | Experimental group 6-L | The postbiotic extract of the present disclosure from Lactobacillus plantarum CB102 | 100 mg/L |
| | Experimental group 6-B | The postbiotic extract of the present disclosure from Bifidobacterium longum CB108 | 200 mg/L |
| Co-culture of Staphylococcus aureus and Bacillus coagulans CB106 | Control group 7 | — | — |
| | Comparative group 7 | Inulin | 5 g/L |
| | Experimental group 7-L | The postbiotic extract of the present disclosure from Lactobacillus plantarum CB102 | 100 mg/L |
| | Experimental group 7-B | The postbiotic extract of the present disclosure from Bifidobacterium longum CB108 | 200 mg/L |

All the groups were cultivated in an incubator (37° C., 5% $CO_2$) for 8 hours. Thereafter, a suitable amount of the respective resultant co-culture was coated onto a MRS agar plate using spread plate technique, followed by cultivation in an incubator (37° C., 5% $CO_2$) overnight. The number of colonies of probiotic microbes on the MRS agar plate of each group was counted, and the log value of the colony forming unit (CFU/mL) was further calculated and the viable cell count was indicated by log CFU/mL.

Results:

Table 7 shows the viable cell count of probiotic microbes in each group. It can be seen from Table 7 that, for the co-culture of Staphylococcus aureus and Lactobacillus acidophilus JCM1132, the increased viable cell counts of probiotic microbes (i.e., Lactobacillus acidophilus JCM1132) determined in the experimental groups 1-L and 1-B were higher than those determined in the comparative group 1 and the control group 1. Besides, similar satisfactory results were observed with respect to the experimental groups 2-L to 7-L and 2-B to 7-B, indicating that the postbiotic extract of the present disclosure can effectively prevent the imbalance of the gut microbiota, and can eliminate or decrease potential or known pathogenic populations in the gut or intestine, and hence is capable of restoring and maintaining a healthy gut microbiota.

TABLE 7

| Group | Test probiotic strain | Increased Viable cell count (log CFU/mL) |
|---|---|---|
| Control group 1 | Lactobacillus acidophilus JCM1132 | 0.8 |
| Comparative group 1 | | 1.1 |
| Experimental group 1-L | | 2.0 |
| Experimental group 1-B | | 1.3 |
| Control group 2 | Lactobacillus casei JCM1134 | 0.5 |
| Comparative group 2 | | 0.8 |
| Experimental group 2-L | | 1.7 |
| Experimental group 2-B | | 1.2 |
| Control group 3 | Lactobacillus plantarum CB102 | 0.4 |
| Comparative group 3 | | 0.7 |
| Experimental group 3-L | | 1.7 |
| Experimental group 3-B | | 1.2 |
| Control group 4 | Bifidobacterium lactis JCM10602 | 0.3 |
| Comparative group 4 | | 0.6 |
| Experimental group 4-L | | 1.8 |
| Experimental group 4-B | | 1.2 |
| Control group 5 | Bifidobacterium bifidum JCM1255 | 0.1 |
| Comparative group 5 | | 0.2 |

TABLE 7-continued

| Group | Test probiotic strain | Increased Viable cell count (log CFU/mL) |
|---|---|---|
| Experimental group 5-L | | 0.8 |
| Experimental group 5-B | | 0.5 |
| Control group 6 | Bifidobacterium | 0.1 |
| Comparative group 6 | longum CB108 | 0.3 |
| Experimental group 6-L | | 0.5 |
| Experimental group 6-B | | 0.4 |
| Control group 7 | Bacillus coagulans | 0.2 |
| Comparative group 7 | CB106 | 0.2 |
| Experimental group 7-L | | 0.6 |
| Experimental group 7-B | | 0.4 |

Example 5. Evaluation for the Effect of Postbiotic Extract According to this Disclosure on Modulating Gut Immunity A. Effect of Postbiotic Extract on TGF-β Content of Caco-2 Cells Caco-2 cells were divided into 25 groups, including one control group, twelve comparative groups (i.e., comparative groups L-1 to L-6 and B-1 to B-6), and twelve experimental groups (i.e., experimental groups L-1 to L-6 and B-1 to B-6). Each group of the Caco-2 cells was incubated in a respective well of a 96-well culture plate containing 200 μL of DMEM at $1\times10^4$ cells/well, followed by cultivation in an incubator (37° C., 5% $CO_2$) for 24 hours. After medium change with a fresh medium, each of the cell cultures of the twelve comparative groups and twelve experimental groups was treated with the respective test postbiotic extract so that the cell culture of each group had a final concentration of the respective test postbiotic extract as shown in Table 8. The cell culture of the control group received no treatment.

TABLE 8

| Group | Test postbiotic extract | Final concentration (mg/L) |
|---|---|---|
| Control group | — | 0 |
| Comparative group L-1 | The postbiotic | 2.5 |
| Comparative group L-2 | extract of the | 5 |
| Comparative group L-3 | prior art from | 25 |
| Comparative group L-4 | Lactobacillus | 50 |
| Comparative group L-5 | plantarum CB102 | 100 |
| Comparative group L-6 | | 200 |
| Experimental group L-1 | The postbiotic | 2.5 |
| Experimental group L-2 | extract of the | 5 |
| Experimental group L-3 | present | 25 |
| Experimental group L-4 | disclosure from | 50 |
| Experimental group L-5 | Lactobacillus | 100 |
| Experimental group L-6 | plantarum CB102 | 200 |
| Comparative group B-1 | The postbiotic | 2.5 |
| Comparative group B-2 | extract of the | 5 |
| Comparative group B-3 | prior art from | 25 |
| Comparative group B-4 | Bifidobacterium | 50 |
| Comparative group B-5 | longum CB108 | 100 |
| Comparative group B-6 | | 200 |
| Experimental group B-1 | The postbiotic | 2.5 |
| Experimental group B-2 | extract of the | 5 |
| Experimental group B-3 | present | 25 |
| Experimental group B-4 | disclosure from | 50 |
| Experimental group B-5 | Bifidobacterium | 100 |
| Experimental group B-6 | longum CB108 | 200 |

After cultivation in an incubator (37° C., 5% $CO_2$) for 24 hours, the respective resultant cell culture was subjected to the determination of TGF-β content according to the method described in section 1 of "General Procedures".

As shown in Table 9 below, the TGF-β contents determined in the experimental groups L-1 to L-6 were respectively higher than those determined in the comparative groups L-1 to L-6, and the TGF-β contents determined in the experimental groups B-1 to B-6 were also respectively higher than those determined in the comparative groups B-1 to B-6. This result suggests that the postbiotic extract of the present disclosure is effective in inducing TGF-β secretion in Caco-2 cells.

TABLE 9

| Group | TGF-β content (pg/mL) |
|---|---|
| Control group | 5.1 |
| Comparative group L-1 | 10.4 |
| Comparative group L-2 | 25.6 |
| Comparative group L-3 | 42.6 |
| Comparative group L-4 | 56.4 |
| Comparative group L-5 | 58.5 |
| Comparative group L-6 | 58.7 |
| Experimental group L-1 | 20.8 |
| Experimental group L-2 | 48.5 |
| Experimental group L-3 | 81.2 |
| Experimental group L-4 | 102.0 |
| Experimental group L-5 | 103.5 |
| Experimental group L-6 | 103.6 |
| Comparative group B-1 | 10.1 |
| Comparative group B-2 | 10.2 |
| Comparative group B-3 | 37.4 |
| Comparative group B-4 | 59.1 |
| Comparative group B-5 | 76.8 |
| Comparative group B-6 | 77.6 |
| Experimental group B-1 | 20.7 |
| Experimental group B-2 | 20.8 |
| Experimental group B-3 | 75.2 |
| Experimental group B-4 | 119.8 |
| Experimental group B-5 | 152.5 |
| Experimental group B-6 | 153.9 |

B. Effect of Postbiotic Extract on TGF-β Content of Caco-2 Cells in the Presence of Gastric Acid A suitable amount of a respective one of Lactobacillus plantarum CB102, Lactobacillus acidophilus JCM1132, Lactobacillus casei JCM1134, Bifidobacterium bifidum JCM1255, Bifidobacterium lactis JCM10602, Bifidobacterium longum CB108, the postbiotic extract of the present disclosure from Lactobacillus plantarum CB102, and the postbiotic extract of the present disclosure from Bifidobacterium longum CB108 was mixed with artificial gastric acid (containing 0.137 M NaCl, 0.0027 M KCl, 0.01 M $Na_2HPO_4$, and 0.0018 M $NaH_2PO_4$, and having a pH of 2), followed by cultivation in an incubator (37° C., 5% $CO_2$) for 3 hours. The resultant mixtures were used for the following experiment and are referred to as "gastric acid-treated" test samples hereinafter.

In addition, Caco-2 cells were divided into 16 groups, including eight comparative groups (i.e., comparative groups 1-8) and eight experimental groups (i.e., experimental groups 1-8). Each group of the Caco-2 cells was incubated in a respective well of a 96-well culture plate containing 200 μL of DMEM at $1\times10^4$ cells/well, followed by cultivation in an incubator (37° C., 5% $CO_2$) for 24 hours. After medium change with a fresh medium, each of the cell cultures of the eight comparative groups and eight experimental groups was treated with the respective test sample so that the cell culture of each group had a final concentration of the respective test sample as shown in Table 10.

TABLE 10

| Group | Test sample | Final concentration |
|---|---|---|
| Comparative group 1 | *Lactobacillus acidophilus* JCM1132 | $1 \times 10^{10}$ CFU/L |
| Experimental group 1 | Gastric acid-treated *Lactobacillus acidophilus* JCM1132 | |
| Comparative group 2 | *Lactobacillus casei* JCM1134 | |
| Experimental group 2 | Gastric acid-treated *Lactobacillus casei* JCM1134 | |
| Comparative group 3 | *Lactobacillus plantarum* CB102 | |
| Experimental group 3 | Gastric acid-treated *Lactobacillus plantarum* CB102 | |
| Comparative group 4 | *Bifidobacterium lactis* JCM10602 | |
| Experimental group 4 | Gastric acid-treated *Bifidobacterium lactis* JCM10602 | |
| Comparative group 5 | *Bifidobacterium bifidum* JCM1255 | |
| Experimental group 5 | Gastric acid-treated *Bifidobacterium bifidum* JCM1255 | |
| Comparative group 6 | *Bifidobacterium longum* CB108 | |
| Experimental group 6 | Gastric acid-treated *Bifidobacterium longum* CB108 | |
| Comparative group 7 | The postbiotic extract of the present dsiclosure from *Lactobacillus plantarum* CB102 | 100 mg/L |
| Experimental group 7 | Gastric acid-treated postbiotic extract of the present disclosure from *Lactobacillus plantarum* CB102 | |
| Comparative group 8 | The postbiotic extract of the present disclosure from *Bifidobacterium longum* CB108 | |
| Experimental group 8 | Gastric acid-treated postbiotic extract of the present disclosure from *Bifidobacterium longum* CB108 | |

After cultivation in an incubator (37° C., 5% $CO_2$) for 24 hours, the respective resultant cell culture was subjected to the determination of TGF-β content according to the method described in section 1 of "General Procedures".

As shown in Table 11 below, the TGF-β contents determined in the experimental groups 1-6 were significantly lower than those determined in the comparative groups 1-6, respectively. However, the TGF-β contents of the experimental groups 7-8 were only slightly decreased as compared to the comparative groups 7-8, respectively, indicating that the postbiotic extract of the present disclosure has an excellent acid tolerance and is able to overcome the environmental pressure posed by the human digestive tract, and hence can reach the intestine (s) and colonize the probiotics therein after ingestion.

TABLE 11

| Group | TGF-ß content (pg/mL) |
|---|---|
| Comparative group 1 | 62.2 |
| Experimental group 1 | 20.1 |
| Comparative group 2 | 112.1 |
| Experimental group 2 | 85.9 |
| Comparative group 3 | 40.6 |
| Experimental group 3 | 31.1 |
| Comparative group 4 | 101.1 |
| Experimental group 4 | 23.6 |
| Comparative group 5 | 143.6 |
| Experimental group 5 | 53.4 |
| Comparative group 6 | 131.7 |
| Experimental group 6 | 42.2 |
| Comparative group 7 | 103.5 |
| Experimental group 7 | 85.5 |
| Comparative group 8 | 154.2 |
| Experimental group 8 | 140.3 |

C. Effect of the Combination of Postbiotic Extract with Probiotics on TGF-β Content of Caco-2 Cells Caco-2 cells were divided into 21 groups, including seven comparative groups (i.e., comparative groups 1-7) and fourteen experimental groups (i.e., experimental groups 1-L to 7-L and 1-B to 7-B). Each group of the Caco-2 cells was incubated in a respective well of a 96-well culture plate containing 200 μL of DMEM at $1 \times 10^4$ cells/well, followed by cultivation in an incubator (37° C., 5% $CO_2$) for 24 hours. After medium change with a fresh medium, the culture of each group was treated with probiotics only or additionally with the postbiotic extract of the present disclosure so that the cell culture of each group respectively had final concentrations of the probiotics only or additionally with the postbiotic extract as shown in Table 12.

TABLE 12

| Group | Probiotic ($1 \times 10^{10}$ CFU/L) | The postbiotic extract of the present disclosure from *Lactobacillus plantarum* CB102 (100 mg/L) | The postbiotic extract of the present disclosure from *Bifidobacterium longum* CB108 (100 mg/L) |
|---|---|---|---|
| Comparative group 1 | *Lactobacillus acidophilus* JCM1132 | − | − |
| Experimental group 1-L | | + | − |
| Experimental group 1-B | | − | + |
| Comparative group 2 | *Lactobacillus casei* JCM1134 | − | − |
| Experimental group 2-L | | + | − |
| Experimental group 2-B | | − | + |
| Comparative group 3 | *Lactobacillus plantarum* CB102 | − | − |
| Experimental group 3-L | | + | − |
| Experimental group 3-B | | − | + |
| Comparative group 4 | *Bifidobacterium lactis* JCM10602 | − | − |
| Experimental group 4-L | | + | − |
| Experimental group 4-B | | − | + |
| Comparative group 5 | *Bifidobacterium bifidum* JCM1255 | − | − |
| Experimental group 5-L | | + | − |
| Experimental group 5-B | | − | + |

TABLE 12-continued

| Group | Probiotic (1 × 10¹⁰ CFU/L) | The postbiotic extract of the present disclosure from *Lactobacillus plantarum* CB102 (100 mg/L) | The postbiotic extract of the present disclosure from *Bifidobacterium longum* CB108 (100 mg/L) |
|---|---|---|---|
| Comparative group 6 | *Bifidobacterium longum* CB108 | − | − |
| Experimental group 6-L | | + | − |
| Experimental group 6-B | | − | + |
| Comparative group 7 | *Bacillus coagulans* CB106 | − | − |
| Experimental group 7-L | | + | − |
| Experimental group 7-B | | − | + |

After cultivation in an incubator (37° C., 5% $CO_2$) for 24 hours, the respective resultant cell culture was subjected to the determination of TGF-β content according to the method described in section 1 of "General Procedures".

As shown in Table 13 below, the TGF-β contents determined in the experimental groups 1-L to 7-L and 1-B to 7-B were respectively higher than those determined in the comparative groups 1-7, indicating that the combination of a postbiotic extract with probiotics is effective in inducing TGF-β secretion in Caco-2 cells.

TABLE 13

| Group | TGF-β content (pg/mL) |
|---|---|
| Comparative group 1 | 20.1 |
| Experimental group 1-L | 100.7 |
| Experimental group 1-B | 155.7 |
| Comparative group 2 | 85.9 |
| Experimental group 2-L | 152.0 |
| Experimental group 2-B | 207.0 |
| Comparative group 3 | 31.1 |
| Experimental group 3-L | 109.3 |
| Experimental group 3-B | 164.3 |
| Comparative group 4 | 23.6 |
| Experimental group 4-L | 103.4 |
| Experimental group 4-B | 158.4 |
| Comparative group 5 | 53.4 |
| Experimental group 5-L | 126.7 |
| Experimental group 5-B | 181.7 |
| Comparative group 6 | 42.2 |
| Experimental group 6-L | 117.9 |
| Experimental group 6-B | 172.9 |
| Comparative group 7 | 52.5 |
| Experimental group 7-L | 126.0 |
| Experimental group 7-B | 181.0 |

Summarizing the above test results, it is clear that the postbiotic extract of the present disclosure has an excellent acid tolerance, and can effectively induce TGF-β secretion in Caco-2 cells, and hence can be used as a food additive for modulating gut immunity.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method of inhibiting biofilm formation, the method comprising applying onto an object a postbiotic extract, wherein the postbiotic extract is prepared by a process including the steps of:
 a) providing a whey protein having an isoelectric point of 4.4 and a dextrin having an isoelectric point of 5.2;
 b) admixing the whey protein and a probiotic bacterium with water having a pH value of 7.5 so as to form a mixture,
 wherein the probiotic bacterium is selected from the group consisting of *Lactobacillus plantarum* CB102, *Lactobacillus acidophilus* JCM1132, *Lactobacillus casei* JCM1134, *Bifidobacterium bifidum* JCM1255, *Bifidobacterium lactis* JCM10602, *Bifidobacterium longum* CB108, and combinations thereof;
 c) adding the dextrin into the mixture, followed by adjusting the pH value of the dextrin-added mixture to between 4.4 and 5.2 so that a precipitate is formed; and
 d) subjecting the precipitate to an acid hydrolysis treatment with lactic acid to isolate the cell wall of the probiotic bacterium, so as to obtain the postbiotic extract;
 wherein the biofilm formation is caused by *Staphylococcus aureus*.

\* \* \* \* \*